United States Patent [19]

Matsunaga et al.

[11] Patent Number: 5,128,007
[45] Date of Patent: Jul. 7, 1992

[54] METHOD FOR EVALUATING A LITHIUM NIOBATE THIN FILM AND APPARATUS FOR PREPARING THE SAME

[75] Inventors: Hironori Matsunaga; Hirotaka Ohno; Yasunari Okamoto, all of Nara, Japan

[73] Assignee: Sharp Kabushiki Kaisha, Osaka, Japan

[21] Appl. No.: 691,502

[22] Filed: Apr. 25, 1991

[30] Foreign Application Priority Data

Apr. 27, 1990 [JP] Japan .................. 2-114434

[51] Int. Cl.$^5$ ............................................. C23C 14/34
[52] U.S. Cl. ........................... 204/192.13; 204/192.15; 204/192.18; 204/192.31; 204/298.03; 204/298.05
[58] Field of Search ............... 204/192.13, 192.33, 204/192.15, 192.18, 192.31, 298.03, 298.05; 118/723, 726; 427/50, 100

[56] References Cited

U.S. PATENT DOCUMENTS

| | | | |
|---|---|---|---|
| 3,734,620 | 5/1973 | Cade | 204/298.03 X |
| 3,988,232 | 10/1976 | Wasa et al. | 204/192.18 |
| 4,140,078 | 2/1979 | Wilmanns | 204/298.03 X |
| 4,166,784 | 9/1979 | Chapin et al. | 204/192.13 X |
| 4,172,020 | 10/1979 | Tisone et al. | 204/192.13 |
| 4,311,725 | 1/1982 | Holland | 204/298.03 X |
| 4,407,709 | 10/1983 | Enjouji et al. | 204/192.13 |

Primary Examiner—Nam Nguyen

[57] ABSTRACT

A method for evaluating a lithium niobate thin film includes measuring an absorption edge wavelength of a lithium niobate thin film and evaluating a lithium-to-niobium composition ratio of the thin film, and an apparatus for preparing a thin film including a thin film-forming body capable of controlling the lithium-to-niobium composition ratio of a lithium niobate thin film being formed and an evaluation device for evaluating the lithium-to-niobium composition ratio, the evaluation device being provided with a monitor substrate, an optical path for spectrometry, an ultraviolet ray source and a measurement part for measuring an absorption edge wavelength of the thin film.

14 Claims, 4 Drawing Sheets

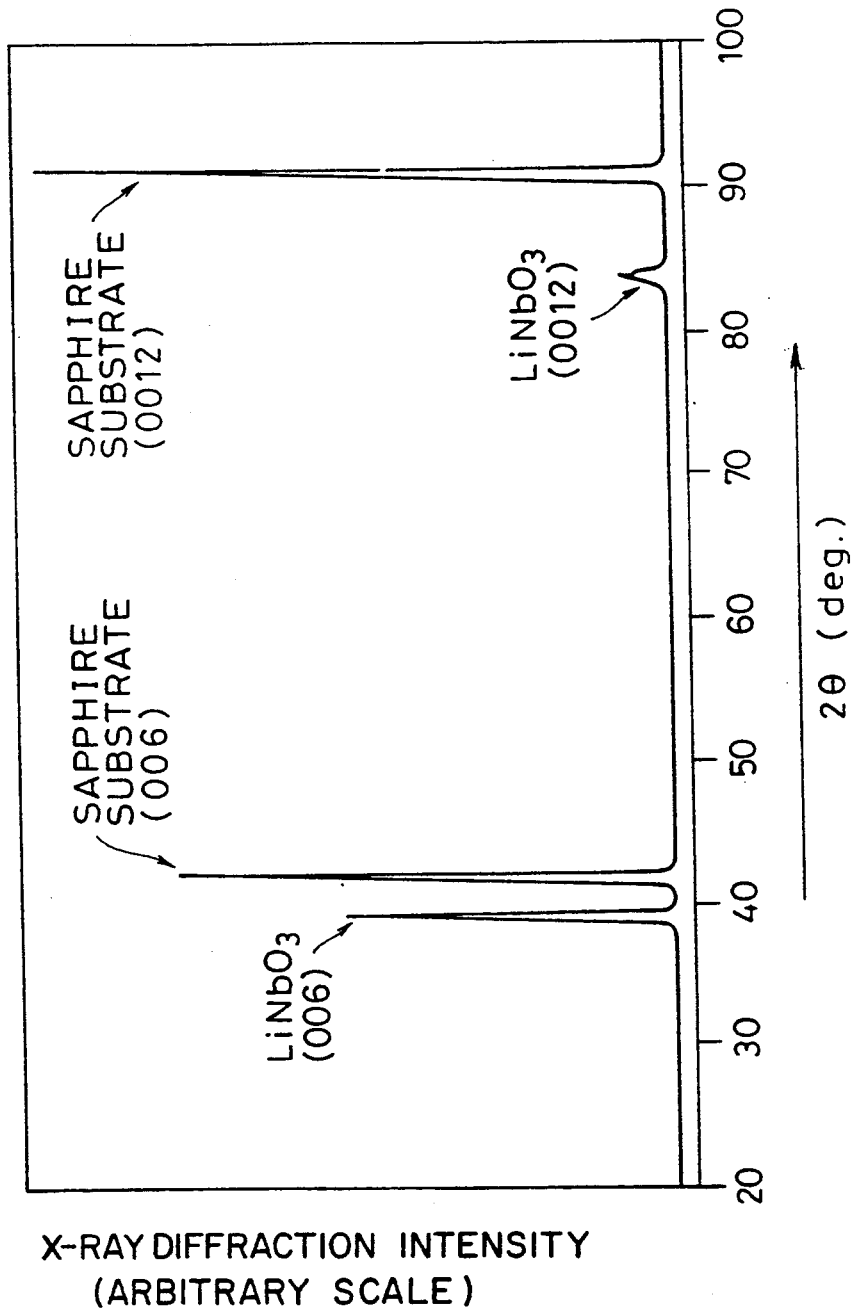

METHOD FOR EVALUATING A LITHIUM NIOBATE THIN FILM AND APPARATUS FOR PREPARING THE SAME

BACKGROUND OF THE INVENTION

1. Field of the Invention

The present invention relates to a method for evaluating a composition ratio of a crystalline lithium niobate ($LiNbO_3$) thin film known as a ferroelectric material by measuring the absorption edge thereof, and to an apparatus for preparing an $LiNbO_3$ thin film capable of controlling conditions for forming an $LiNbO_3$ thin film while monitoring the film being formed by the use of the above method.

2. Prior Arts

Among various ferroelectric oxides, $LiNbO_3$ is particularly characterized by its high melting point, its high Curie temperature and good chemical stability. Accordingly $LiNbO_3$ is widely used in various fields as a material for optical integrated circuits, surface elastic wave devices and the like which utilize electrooptic effects, non-linear optic effects, piezoelectric effects or the like. Further, for the purpose of making good use of the properties of this material and of minimizing the prices of developed devices and the like, development of devices using an $LiNbO_3$ thin film is under way, and a technique for preparing an $LiNbO_3$ thin film is needed.

An $LiNbO_3$ thin film is formed using sputtering, ion plating or CVD method. Usually a hetero-epitaxial single-crystalline $LiNbO_3$ film is formed on a single-crystalline substrate of $\alpha$-$Al_2O_3$, MgO, ZnO or the like, while a polycrystalline $LiNbO_3$ film is formed on a glass- or polycrystalline ceramic substrate.

However, in the case of preparing $LiNbO_3$ thin films as described above, it is necessary to develop a method for efficiently evaluating the stoichiometrical composition ratio of an $LiNbO_3$ thin film. Evaluation of the stoichiometrical ratio is meant here to evaluate whether or not Li/Nb composition ratio of an $LiNbO_3$ thin film is 1. As well, it is necessary to establish a method for preparing an $LiNbO_3$ thin film with a good reproducibility of the stoichiometrical ratio.

In the case of forming an $LiNbO_3$ film by sputtering or ion plating, the vapor pressure of Li is extremely high relative to that of Nb, and hence it has been difficult to establish conditions for forming uniform $LiNbO_3$ thin films of the stoichiometrical ratio (Li/Nb=1). Therefore, a film formation test taking a lengthy period of time has been required.

The above film formation test has been carried out every time a thin film preparing apparatus or film-forming conditions are changed. For example, the composition ratio of a target is changed in the test using sputtering, while the deposition ratio of Li to Nb is changed in the test using ion plating.

Further, a composition ratio of the thus formed thin film has been measured by means of Secondary Ion Mass Spectrometer (SIMS), Auger Electron Spectrometer (AES) or the like, and hence it has taken a long period of time to analyze. These apparatus cannot avoid destructive analysis and at the same time have difficulties in analyzing insulating materials. Furthermore, they are expensive and hard to manipulate.

Accordingly, the analysis of $LiNbO_3$ thin films has been a bottleneck in repeatedly performing the film formation test for optimizing the film-forming conditions. Hence, a method capable of evaluating a composition ratio of the thin film in a short period of time has been required.

SUMMARY OF THE INVENTION

To overcome the abovementioned problems, an object of the invention is to provide a method for efficiently evaluating a composition ratio of an $LiNbO_3$ thin film.

A further object of the invention is to provide an apparatus capable of preparing an $LiNbO_3$ thin film having a uniform composition ratio.

Thus, the present invention provides a method for evaluating a lithium niobate thin film, comprising measuring an absorption edge wavelength of a lithium niobate thin film and evaluating a lithium-to-niobium composition ratio of the thin film.

Further, the invention provides an apparatus for preparing a thin film, comprising a thin film-forming body capable of controlling a lithium-to-niobium composition ratio of a lithium niobate thin film to be formed, and an evaluation device for evaluating the lithium-to-niobium composition ratio, the evaluation device being provided with a monitor substrate, an optical path for spectrometry, an ultraviolet ray source and a measurement part for measuring an absorption edge wavelength.

BRIEF DESCRIPTION OF THE DRAWINGS

FIG. 4 is an X-ray diffraction pattern of the $LiNbO_3$ thin film prepared in the embodiment.

DETAILED DESCRIPTION OF THE PREFERRED EMBODIMENTS

The present invention utilizes the fact that the absorption edge varies susceptibly to a composition ratio variation of an $LiNbO_3$ film in the vicinity of its stoichiometrical ratio, and evaluates a composition ratio of a thin film on the basis of measurement of the absorption edge.

To effect the present invention, many lithium niobate thin films of different composition ratios are previously prepared and which are then subjected to SIMS or the like for measuring their Li-to-Nb composition ratios. The absorption edge of each of the films in the ultraviolet region is also measured for preparing correlated data between the Li-to-Nb composition ratios and absorption edges. Then, a newly formed $LiNbO_3$ thin film is quickly evaluated with respect to its composition ratio while referring to its absorption edge to the correlated data.

Since the above evaluation of an Li-to-Nb composition ratio can be quickly performed in a non-destructive manner, it is possible to measure a composition ratio of an $LiNbO_3$ film being formed. Hence, according to the invention it becomes possible to quickly determine film-forming conditions under which an $LiNbO_3$ thin film of the stoichiometrical composition ratio can be formed, by monitoring a composition ratio of an LiNbO₃ thin film being formed. As a result, LiNbO₃ thin films can be efficiently prepared.

Figure 2:
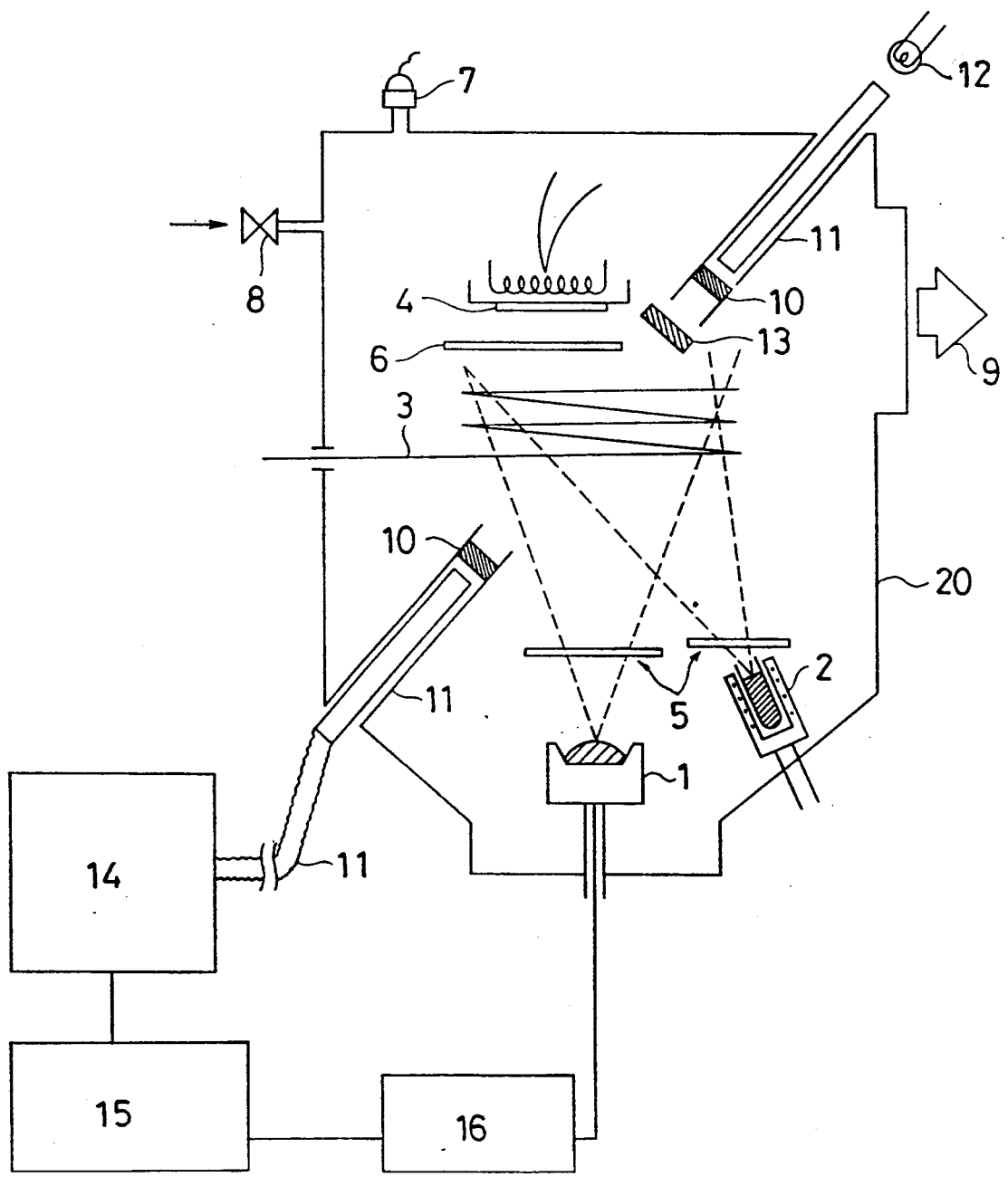
FIG. 2 is a sectional view schematically illustrating a thin-film preparing apparatus of an embodiment according to the invention.

An apparatus as shown in FIG. 2 was used in the following examples for forming LiNbO₃ films.

PREPARATION OF CORRELATED DATA BETWEEN COMPOSITION RATIO AND ABSORPTION EDGE

A vacuum chamber 20 as shown in FIG. 2 incorporating an evaporation source 1 heated with an electron beam, a Knudsen cell 2, a high-frequency working coil 3 for generating plasma and the like was evacuated to about $1 \times 10^{-8}$ Torr by means of a vacuum pump connected to an exhaust outlet 9 of the chamber 20. Thereafter, oxygen gas was introduced therein but only to around the coil 3 through a valve 8 up to $2 \times 10^{-4}$ Torr and which was made into plasma by being applied with Rf power (13.56 MHz, 200 W) by means of the coil 3.

Under the conditions of the chamber 20 as above, a thin film was formed on a substrate 4 (Corning 7059 glass) as heated to and maintained at 400° C. by simultaneously depositing Nb and Li vapors which were respectively produced from Nb (purity: 4N) disposed in the evaporation source 1 and from Li (purity: 4N) disposed in the Knudsen cell 2 by individually controlled heating, and which were then passed through the oxygen plasma atmosphere. In this example the deposition rate of Nb was fixed to 10 Å/min. while that of Li was varied within the range of 10–30 Å/min. The eventual thickness of the film was designed to be about 3000 Å.

Figure 1:
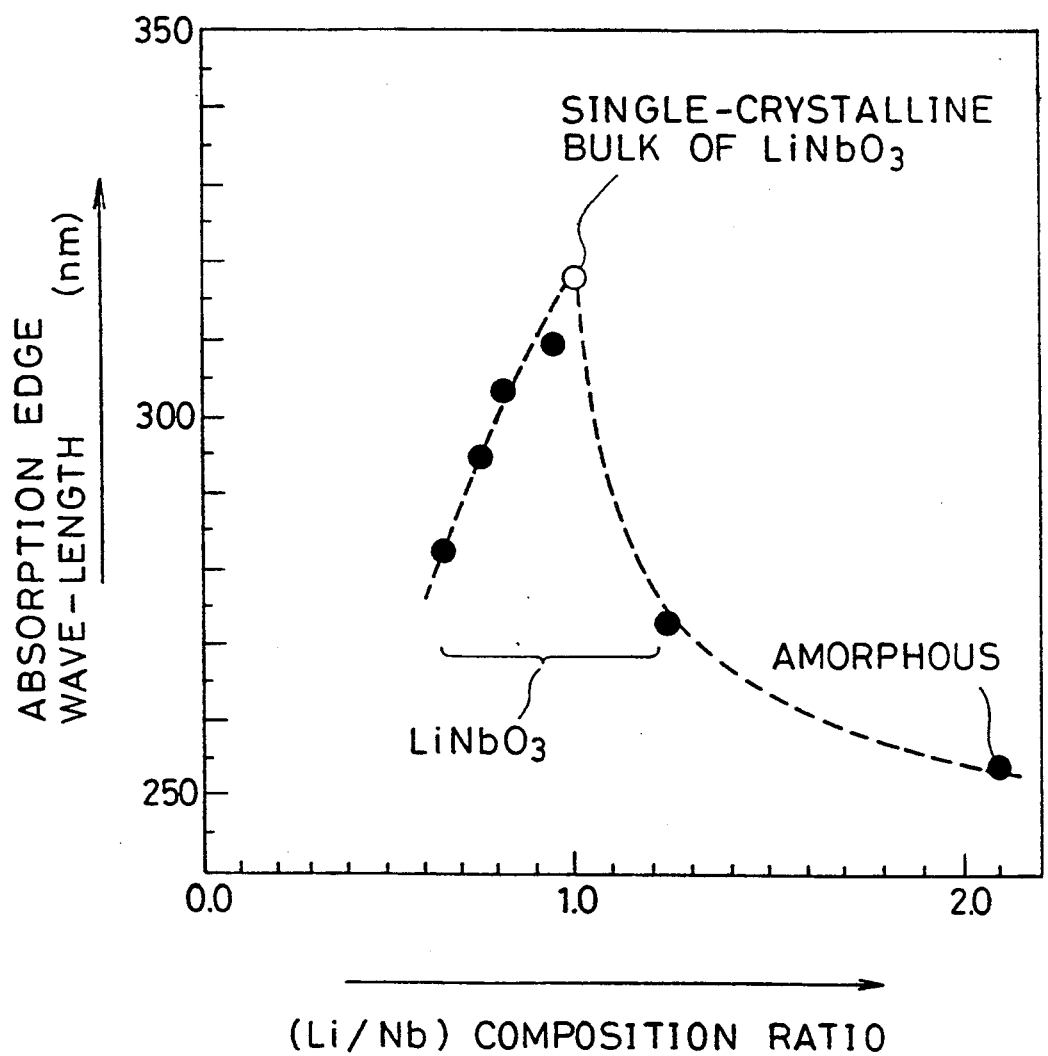
FIG. 1 is a graph showing a relationship between an Li-to-Nb composition ratio and absorption edge of an $LiNbO_3$ thin film prepared in an embodiment of the invention.

With respect to the thus prepared thin film, the composition ratio was measured using X-ray diffraction and SIMS while the absorption edge was measured using a visible-ultraviolet Spectrophotometer. A black point in FIG. 1 represents the correlation between the composition ratio and the absorption edge. For reference indicated at a white point in FIG. 1 is a measured value of a single-crystalline bulk of LiNbO₃.

FIG. 1 reveals the following facts:
(1) The absorption edge grows longest at the stoichiometrical ratio (Li/Nb=1);
(2) Excess of Li causes the absorption edge to be shortened sharply;
(3) The absorption edge is also shortened in the Nb-excess area; and
(4) In the X-ray diffraction, the LiNbO₃ diffraction pattern is obtained in a relatively wide composition range near the point of Li/Nb=1.

From the above facts, it can be said that obtaining the LiNbO₃ diffraction pattern does not always indicate that the entire film has the stoichiometrical ratio. On the other hand, the Li-to-Nb composition ratio determines the absorption edge, and hence whether a film-forming condition is proper or not can be judged on the basis of whether the absorption edge of the obtained film falls within 310–320 nm, even if the film-forming conditions such as the deposition rates of Li and Nb are changed.

Accordingly, in the case of monitoring a composition variation of an LiNbO₃ thin film formed as in the method of this example but under the different film-forming conditions and also in the case of fixing film-forming conditions in a different film-formation method, an obtained thin film can be quickly judged to have the optimal composition ratio (Li/Nb=1) or not by measuring its absorption edge and referring it to FIG. 1 obtained in this example.

MONITORING THE COMPOSITION RATIO OF A FILM BEING FORMED

An apparatus for preparing an LiNbO₃ was manufactured by providing the vacuum chamber of the former example with a visible-ultraviolet Spectrophotometer capable of measuring spectral characteristics in the visible-ultraviolet region on the basis of which a composition of an LiNbO₃ thin film being formed could be evaluated. Then, an LiNbO₃ thin film was prepared using the thus manufactured apparatus.

The schematic sectional view of the apparatus is shown in FIG. 2. In this figure an optical path 11 for spectrometry in which a monitor quartz substrate 13 and a quartz window 10 are disposed is provided for the vacuum chamber 20 described in the former example. Incidentally, the reference numeral 7 denotes a vacuum gauge.

An oxygen plasma atmosphere was produced in the vacuum chamber 20 as in the same manner described in the former example. Then, Li placed in the Knudsen cell 2 was heated to 560° C. and emission current for the evaporation source 1 for Nb was set to 100 mA to render the evaporation states of Li and Nb constant. Shutters 5 for both of the evaporation source were opened to perform simultaneous deposition of Li and Nb on the monitor quartz substrate 13. During this monitoring deposition, light from a light source was allowed to transmit the quartz substrate 13 and the absorption edge of the thin film being formed was measured using a spectrometer 14 capable of measuring visible-ultraviolet region. Although luminescence of the oxygen plasma acted as a background of spectrum of the light transmitted through the substrate, the absorption edge could easily be specified from the shape of the spectrum. In this case the measured absorption edge was 270 nm. Under control of a computer 15 output of a power controller 16 of the evaporation source 1 was increased for raising the emission current so that the absorption edge could fall within the range of about 310–320 nm which was the absorption edge range of an LiNbO₃ thin film of the stoichiometrical composition ratio. Consequently, when the emission current was 170 mA, the absorption edge of the thin film being monitored indicated 310 nm.

The reason why the composition ratio can be monitored while the evaporation sources are being controlled is that the absorption edge grows shorter as the composition ratio of the thin film deviates from the stoichiometrical ratio (Li/Nb=1). If the absorption edge of the LiNbO₃ thin film grew longer as the composition ratio thereof deviated from the stoichiometrical ratio (Li/Nb=1), the absorption edge would become longer than 320 nm under the film-forming conditions initially set. The measured absorption edge of the thin film being monitored would not become shorter even if the conditions were thereafter changed so that the composition ratio of the film might approximate to the stoichiometrical ratio (Li/Nb=1). Accordingly, the values measured in this case do not form a basis for adjustment of the film-forming conditions.

In this example, the film-forming conditions such as of the evaporation sources were maintained as when the absorption edge of the monitored thin film indicated 310 nm, another thin film was deposited on a sapphire substrate 4 (Z face, substrate temperature: 600° C.) for 2 hours by opening a shutter 6. The resulting LiNbO₃ film was 4000 Å thick and of which composition distribution and crystallinity were measured by means of SIMS and X-ray diffraction.

Figure 3:
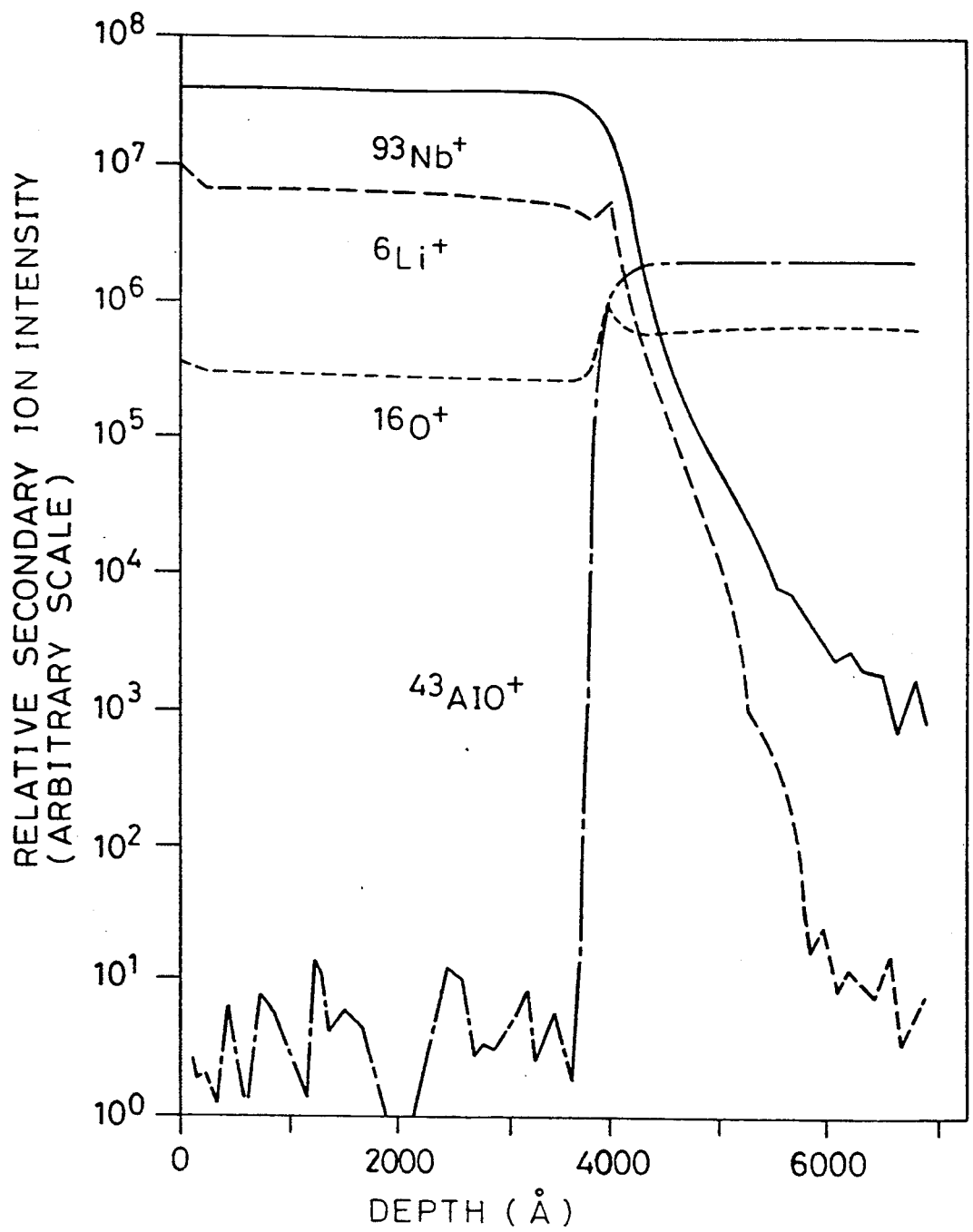
FIG. 3 is a distribution pattern of a composition measured by SIMS in terms of the film-growth direction of the $LiNbO_3$ thin film prepared in the embodiment according to the invention.

FIG. 3 shows a composition distribution of Nb and Li of the thus formed thin film in terms of film-growing direction. As can be understood from FIG. 3, the composition distribution in terms of film-growing direction was uniform and a relative secondary ion intensity ratio of Nb and Li agreed well to that of a single-crystalline bulk of $LiNbO_3$.

Further, FIG. 4 shows an X-ray diffraction pattern of the $LiNbO_3$ thin film for examining the crystallinity thereof. As shown in FIG. 3 only observed was an X-ray diffraction pattern of $LiNbO_3$ of Z face and thus it was confirmed that the $LiNbO_3$ was epitaxially grown on the sapphire substrate of Z face.

While the present invention has been described in detail with reference to the preferred embodiments which are not limitative of the invention, certain changes or modifications can be made without departing from the scope of the invention. For instance, although the absorption edge of the thin film was measured using light transmitted through the film in the present embodiments, it is possible to use reflected light from the film for measuring the same. Further, although the deposition rate of Nb was controlled to vary while that of Li was made constant in order to obtain the $LiNbO_3$ thin film of the stoichiometrical composition ratio in the present embodiments, it is possible to form the thin film in a reverse manner, that is, the deposition rate of Nb is made constant while that of Li is controlled to vary. Still further, a Knudsen cell and an evaporation source heated with electron beam were used as evaporation sources in the present embodiments, any evaporation means may be used in combination with the method of the present embodiments or another provided that the required deposition rate can be attained.

What is claimed is:

1. An apparatus for forming a lithium niobate thin film comprising:
    a vacuum chamber at a predetermined pressure;
    a high frequency coil, located in said vacuum chamber;
    means for introducing oxygen gas into said vacuum chamber near said high frequency coil;
    said high frequency coil generating an oxygen plasma atmosphere by applying Rf power of a predetermined frequency and wattage to said high frequency coil;
    a substrate located within said vacuum chamber;
    means for heating said substrate to a predetermined temperature;
    evaporation means, operating at a predetermined current, for producing niobium vapor;
    means for producing lithium vapor;
    means for passing the lithium vapor and niobium vapor through the oxygen plasma atmosphere;
    means for simultaneously depositing the lithium vapor and niobium vapor on said substrate to form a lithium niobate thin film;
    means for measuring an absorption edge wavelength of the lithium niobate thin film; and
    means for controlling the predetermined pressure of said vacuum chamber, the predetermined frequency and wattage of the Rf power, the predetermined temperature of said substrate, the predetermined current of said evaporation means, a deposition rate of the lithium vapor and a deposition rate of the niobium vapor such that the absorption edge wavelength falls within a predetermined range.

2. The apparatus for forming a lithium niobate thin film of claim 1, wherein the predetermined range for the absorption edge wavelength is 310-320 nm.

3. The apparatus for forming a lithium niobate thin film of claim 2, wherein the deposition rate of lithium vapor is 10-30 Å/min and the deposition rate of niobium vapor is 10 Å/min.

4. The apparatus for forming a lithium niobate thin film of claim 3, wherein the predetermined current of said evaporation means is 100 mA.

5. The apparatus for forming a lithium niobate thin film of claim 4, wherein the predetermined temperature of said substrate is 400° C.

6. The apparatus for forming a lithium niobate thin film of claim 5, wherein the predetermined frequency and wattage of the Rf power applied by said high frequency coil is 13.56 MHz and 200 W, respectively.

7. The apparatus for forming a lithium niobate thin film of claim 6, wherein the predetermined vacuum pressure of said vacuum chamber is $1 \times 10^{-8}$ Torr.

8. A method for forming a lithium niobate thin film, comprising the steps of:
    (a) pressurizing a vacuum chamber at a predetermined pressure;
    (b) introducing oxygen gas into the vacuum chamber near a high frequency coil;
    (c) applying Rf power of a predetermined frequency and wattage to the high frequency coil to generate an oxygen plasma atmosphere;
    (d) heating a substrate to a predetermined temperature;
    (e) producing niobium vapor, utilizing an evaporator operating at a predetermined current;
    (f) producing lithium vapor;
    (g) passing the lithium vapor and niobium vapor through the oxygen plasma atmosphere;
    (h) simultaneously depositing the lithium vapor and niobium vapor on the substrate to form a lithium niobate thin film;
    (i) measuring an absorption edge wavelength of the lithium niobate thin film; and
    (j) controlling the predetermined pressure of the vacuum chamber, the predetermined frequency and wattage of the Rf power, the predetermined temperature of the substrate, the predetermined current of the evaporator, a deposition rate of the lithium vapor and a deposition rate of the niobium vapor such that the absorption edge wavelength falls within a predetermined range.

9. The method for forming a lithium niobate thin film of claim 8, wherein the predetermined range for the absorption edge wavelength is 310-320 nm.

10. The method for forming a lithium niobate thin film of claim 9, wherein the deposition rate of lithium vapor is 10-30 Å/min and the deposition rate of niobium vapor is 10 Å/min.

11. The method for forming a lithium niobate thin film of claim 10, wherein the predetermined current of the evaporator is 100 mA.

12. The apparatus for forming a lithium niobate thin film of claim 11, wherein the predetermined temperature of the substrate is 400° C.

13. The apparatus for forming a lithium niobate thin film of claim 12, wherein the predetermined frequency and wattage of the Rf powers applied to the oxygen gas is 13.56 MHz and 200 W, respectively.

14. The apparatus for forming a lithium niobate thin film of claim 13, wherein the predetermined vacuum pressure of the vacuum chamber is $1 \times 10^{-8}$ Torr.

* * * * *